US010471248B2

United States Patent
Kunschak et al.

(10) Patent No.: US 10,471,248 B2
(45) Date of Patent: Nov. 12, 2019

(54) MEDICAL FLUID CONTROL DEVICE FOR A MEDICAL FLUID LINE SYSTEM

(71) Applicant: B. Braun Melsungen AG, Melsungen (DE)

(72) Inventors: Ralf Kunschak, Willisau (CH); Sebastian Bieri, Schüptheim (CH); Martin Schneider, Thun (CH); Mayur Dudhane, Escholzmatt (CH); Frank Eisen, Escholzmatt (CH); Fritz Kobel, Hettiswil (CH)

(73) Assignee: B. Braun Melsungen AG (DE)

( * ) Notice: Subject to any disclaimer, the term of this patent is extended or adjusted under 35 U.S.C. 154(b) by 0 days.

(21) Appl. No.: 15/561,152

(22) PCT Filed: Mar. 9, 2016

(86) PCT No.: PCT/EP2016/055024
§ 371 (c)(1),
(2) Date: Sep. 25, 2017

(87) PCT Pub. No.: WO2016/150707
PCT Pub. Date: Sep. 29, 2016

(65) Prior Publication Data
US 2018/0050187 A1 Feb. 22, 2018

(30) Foreign Application Priority Data
Mar. 26, 2015 (DE) .......................... 10 2015 205 517

(51) Int. Cl.
*A61M 39/22* (2006.01)
*A61M 39/10* (2006.01)
(Continued)

(52) U.S. Cl.
CPC .......... *A61M 39/225* (2013.01); *A61M 39/10* (2013.01); *A61M 39/22* (2013.01);
(Continued)

(58) Field of Classification Search
CPC ............ A61M 2039/229; A61M 39/10; A61M 39/1011; A61M 39/22; A61M 39/24;
(Continued)

(56) References Cited

U.S. PATENT DOCUMENTS 3,008,491 A * 11/1961 Riefler ................ F16K 11/0836
137/625.19
4,130,128 A * 12/1978 Kaneko ................. F16K 5/0605
137/269
(Continued)

FOREIGN PATENT DOCUMENTS

CN 103596619 A 2/2014
CN 103889500 A 6/2014
(Continued)

OTHER PUBLICATIONS

International Search Report and Written Opinion for International Application PCT/EP2016/055024, dated Apr. 25, 2016—8 Pages.
(Continued)

*Primary Examiner* — Nathan R Price
*Assistant Examiner* — Mark Alan Igel
(74) *Attorney, Agent, or Firm* — RatnerPrestia

(57) ABSTRACT

A medical fluid control device for a medical fluid line system includes a fluid flow housing with at least one connection port for connecting to a further functional component of the fluid line system and which has an injection port with an openable closure element, and also having an adjustment member which is mounted movably in the fluid flow housing and which has flow channel sections which, depending on an adjustment position of the adjustment member, can be moved toward the at least one connection port and/or the injection port for a fluid throughflow. Assigned to at least one flow channel section of the adjustment member and/or to the injection port is at least one mechanical flow accel-
(Continued)

Figure 1:
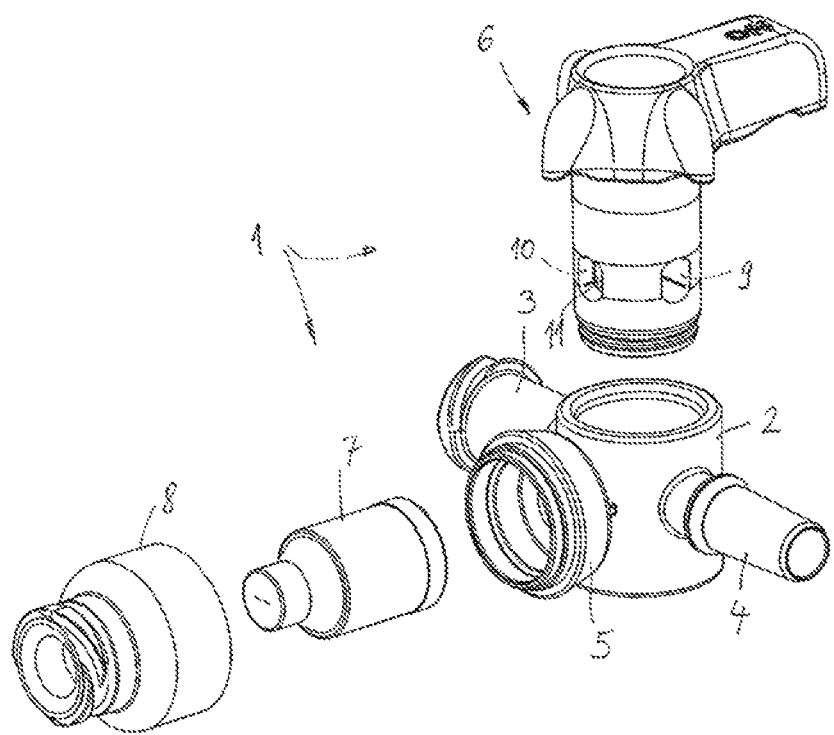

eration mechanism which assists with inside flushing of the injection port during a fluid throughflow.

10 Claims, 7 Drawing Sheets

(51) Int. Cl.
  *F16K 11/085* (2006.01)
  *F16K 15/14* (2006.01)
  *A61M 39/26* (2006.01)

(52) U.S. Cl.
  CPC ........ *F16K 11/0853* (2013.01); *F16K 15/147* (2013.01); *A61M 39/26* (2013.01); *A61M 2039/229* (2013.01)

(58) Field of Classification Search
  CPC .............. A61M 39/223; A61M 39/225; A61M 5/16813; F16K 11/0853; F16K 15/147; F16K 5/0407; F16K 5/10; F16K 5/12; Y10T 137/86566; Y10T 137/86871
  See application file for complete search history.

(56) References Cited

U.S. PATENT DOCUMENTS

| | | | | |
|---|---|---|---|---|
| 4,517,844 | A * | 5/1985 | Powell | G01L 19/0023 600/485 |
| 4,714,092 | A * | 12/1987 | Sanders | F16K 5/0605 137/625.47 |
| 5,135,026 | A * | 8/1992 | Manska | A61M 39/22 137/555 |
| 6,974,116 | B1 * | 12/2005 | Christenson | F16K 5/0605 137/625.32 |
| 7,984,730 | B2 * | 7/2011 | Ziv | A61M 39/223 137/239 |
| 8,702,661 | B2 | 4/2014 | Hornig et al. | |
| 8,843,679 | B2 | 9/2014 | Toba et al. | |
| 9,061,129 | B2 | 6/2015 | Lauer | |
| 9,669,207 | B2 * | 6/2017 | Ueda | F16K 11/0873 |
| 9,694,139 | B2 | 7/2017 | Shaw et al. | |
| 2001/0013370 | A1 * | 8/2001 | Loo | A61M 39/223 137/625.47 |
| 2007/0068587 | A1 * | 3/2007 | Utterberg | F16K 5/0414 137/872 |
| 2011/0175347 | A1 * | 7/2011 | Okiyama | A61J 1/2089 285/132.1 |
| 2011/0282303 | A1 | 11/2011 | Hornig et al. | |
| 2012/0065502 | A1 | 3/2012 | Levy et al. | |
| 2013/0030348 | A1 | 1/2013 | Lauer | |
| 2015/0190623 | A1 * | 7/2015 | Ueda | A61M 39/045 604/246 |
| 2015/0297823 | A1 | 10/2015 | Levy et al. | |
| 2015/0297880 | A1 | 10/2015 | Ogawa et al. | |
| 2017/0348468 | A1 * | 12/2017 | Kana | A61M 1/0035 |
| 2017/0368254 | A1 | 12/2017 | Levy et al. | |

FOREIGN PATENT DOCUMENTS

| | | | |
|---|---|---|---|
| DE | 102006044722 A1 | 4/2008 | |
| EP | 0410898 A2 | 7/1990 | |
| EP | 1970650 A2 * | 9/2008 | ............... F16K 5/10 |
| EP | 2808586 A1 | 12/2014 | |
| RU | 2010154095 A | 7/2012 | |
| WO | 2007084214 A1 | 7/2007 | |
| WO | 2010083962 A1 | 7/2010 | |
| WO | 2014049810 A1 | 4/2014 | |
| WO | 2014049826 A1 | 4/2014 | |
| WO | 2013146753 A1 | 12/2015 | |

OTHER PUBLICATIONS

German Search Report for German Application No. 10 2015 205 517.5, dated Oct. 12, 2015—9 Pages.
Chinese Office Action with Search Report for Chinese Application No. 201680018488.8, dated Dec. 14, 2018, with translation, 18 pages.
Russian Office Action with Search Report for Russian Application No. 2017133810/14, dated Jul. 25, 2019, with translation, 10 pages.

\* cited by examiner

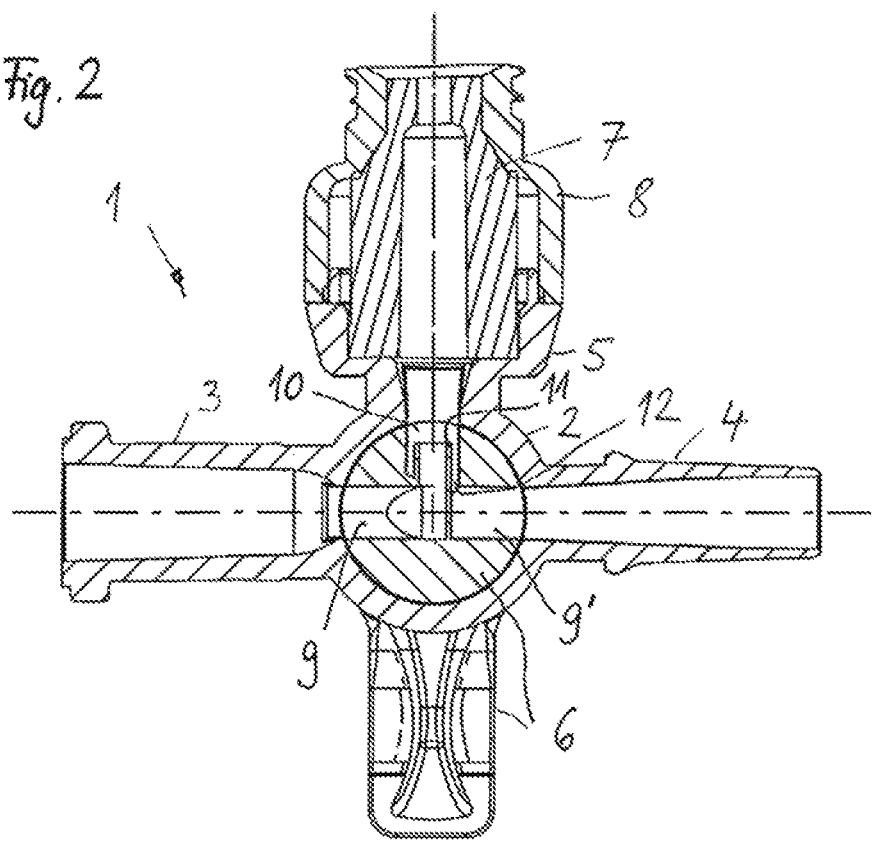
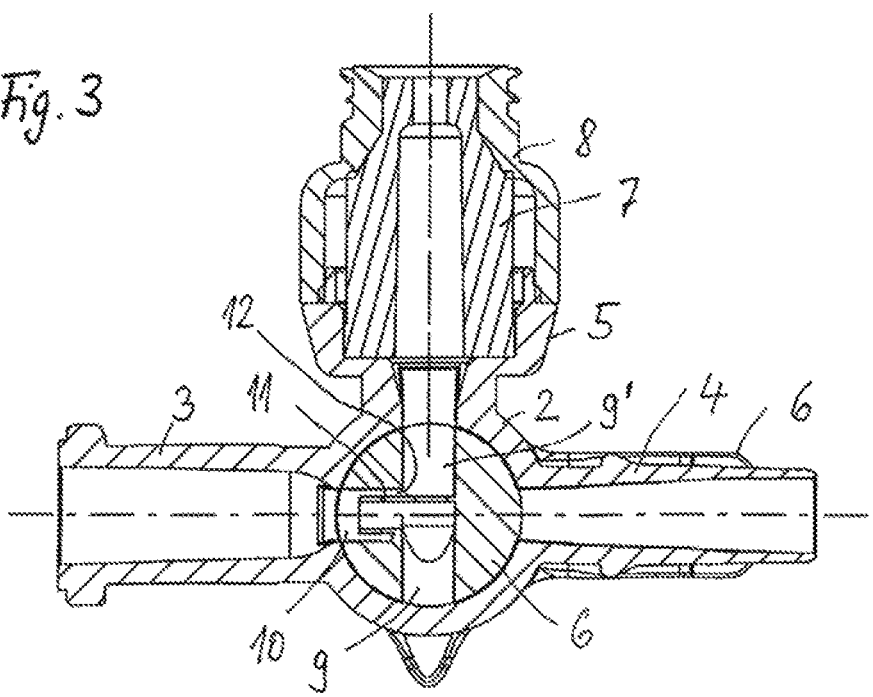

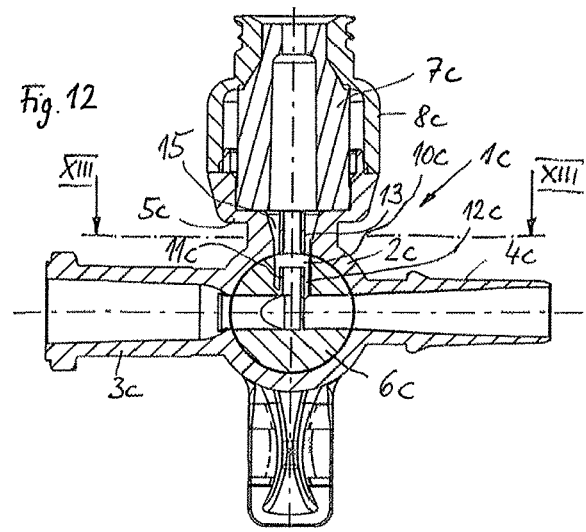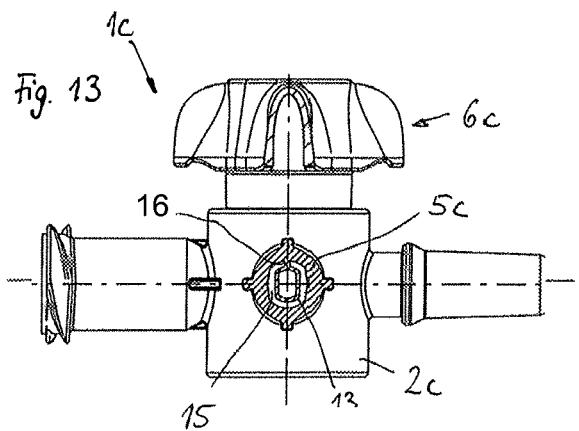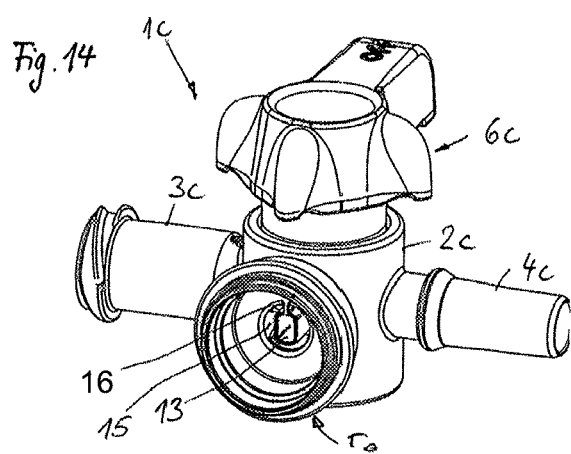

MEDICAL FLUID CONTROL DEVICE FOR A MEDICAL FLUID LINE SYSTEM

RELATED APPLICATIONS

This application is the United States national phase entry of International Application No. PCT/EP2016/055024, filed Mar. 9, 2016, which is related to and claims the benefit of priority of German Application No. DE 10 2015 205517.5, filed Mar. 26, 2015. The contents of International Application No. PCT/EP2016/055024 and German Application No. DE 10 2015 205517.5 are incorporated by reference herein in their entirety.

FIELD

The invention relates to a medical fluid control device for a medical fluid line system, comprising a fluid flow housing which is provided with at least one connection port for connecting to a further functional component of the fluid line system and which has an injection port which is provided with an openable closure element, and also comprising an adjustment member which is mounted movably in the fluid flow housing and which has flow channel sections which, in dependence on an adjustment position of the adjustment member, can be moved toward the at least one connection port and/or the injection port for a fluid throughflow.

BACKGROUND

Such a medical fluid control device is known from U.S. Pat. No. 7,984,730 B2. The known medical fluid control device is designed as a three-way stopcock for a medical infusion system. The three-way stopcock has two connection ports and one injection port which are all formed integrally on a fluid flow housing. The injection port is provided with an openable closure element in the form of a closure cap, which can be fitted by way of a Luer lock connection, or in the form of an elastically flexible closure diaphragm. The closure cap can be twisted off and removed from the injection port. The closure diaphragm is openable in that it can be opened in an elastic manner in the region of an end-side throughflow slot. The closure diaphragm is opened in particular by the attachment of an injector. The fluid flow housing has an adjustment member which is mounted rotationally movably in the fluid flow housing and which is provided with flow channel sections which, depending on the position of the adjustment member, are in fluidic connection, that is to say in throughflow connection, with the two connection ports or with at least one connection port and the injection port. When the closure element is closed, that is to say when the injection port is closed, it is thus possible to divert via the injection port a fluid throughflow in the region of the connection ports and thus bring about flushing of an inner side of the injection port. Consequently, the unwanted deposition of medicament residues in the injection port can be avoided.

SUMMARY

It is the object of the invention to provide a medical fluid control device of the type mentioned at the beginning which allows particularly accurate dosing of medicament for a patient.

Said object is achieved in that assigned to at least one flow channel section of the adjustment member and/or to the injection port is at least one mechanical flow acceleration means which assists with inside flushing of the injection port during a fluid throughflow. As a result, in comparison with the prior art, further improved flushing of the inside of the injection port is achieved. According to the invention it is therefore ensured that, during administration of medicament in the region of the injection port, no medicament residues remain in the region of the injection port, and so a dose of medicament fed via the injection port can pass in its entirety into a patient line of the medical fluid line system and consequently allows highly accurate dosing of medicament for the patient. Moreover, deposition is avoided by the permanent flushing of the lateral connection port/injection port. The mechanical flow acceleration means bring about an increase in speed of the fluid flow guided through the at least one connection port and the injection port, whereby the fluid flow is necessarily able to bring about a relatively high flushing performance in the region of the inside of the injection port. Mechanical flow guiding means which realize a narrowing of a flow cross section for the fluid throughflow in the at least one flow channel section are preferably provided as mechanical flow acceleration means. The flow acceleration means may have a nozzle function. Alternatively or additionally, provision is made to form at least one flow acceleration means by way of swirl-generating means on wall regions of the at least one flow channel section, which swirl-generating means exert a swirling effect on the fluid throughflow and consequently likewise realize an acceleration in particular of wall-side fluid-flow regions. The solution according to the invention is suitable in a particularly advantageous manner for use in a medical fluid line system in the form of an infusion system. Particularly advantageously, the solution according to the invention is usable in an infusion system for administering cytostatic agents. The openable closure element in the context of the invention is preferably designed either as a closure cap which is connectable to the injection port via a Luer lock connection or as an elastically flexible closure diaphragm which is integrated into the injection port.

In one configuration of the invention, the mechanical flow acceleration means is formed by a tube section which is integrated into the flow channel section and/or into the injection port and whose flow cross section is smaller than a flow cross section of a flow channel section, adjacent upstream, of the adjustment member or of the injection port or of the connection port. This results in a tube-in-tube configuration which ensures acceleration of the fluid throughflow because of the reduced flow cross section of the tube section. If within the flow channel section the tube section is positioned so as to be exposed, a backflow of the fluid throughflow on the outside of the tube section to a connection port located correspondingly downstream is made possible. If according to a variant of this configuration there is respectively one tube section in the flow channel section and the injection port, the tube sections that are adjacent—which depends on the position of the adjustment member—are preferably alignable so as to be coaxial with respect to one another. The adjacent tube sections preferably have identical tube cross sections. The at least one tube section serves to guide the fluid throughflow into the interior of the injection port with increased flow speed as soon as the adjustment member has assumed a corresponding adjustment position.

In a further configuration of the invention, the tube section is formed integrally in the flow channel section of the adjustment member or in the injection port of the fluid flow housing. Here, the tube section is preferably connected via integrally formed radial or circumferential ribs to a corresponding inner wall of the flow channel section or of the injection port.

In a further configuration of the invention, an annular gap allowing a fluid throughflow is provided between an outer wall of the tube section and a wall of the flow channel section or an inner wall of the injection port. Preferably, the annular gap is provided as a partial annular section only over a partial region of a circumference of the tube section in order not to adversely affect the integral connection of the tube section to at least one wall of the flow channel section or to an inner wall of the injection port.

In a further configuration of the invention, an inner wall of the tube section is provided with swirl-generating geometries which act on the fluid throughflow. The swirl-generating geometries, which are preferably formed integrally in the region of the inner wall of the tube section, allow further improved accelerations of the fluid throughflow. The swirl-generating geometries preferably disturb a laminar flow of the fluid throughflow at the inner wall of the tube section and thus allow flow acceleration.

BRIEF DESCRIPTION OF THE DRAWING FIGURES

Figure 4:
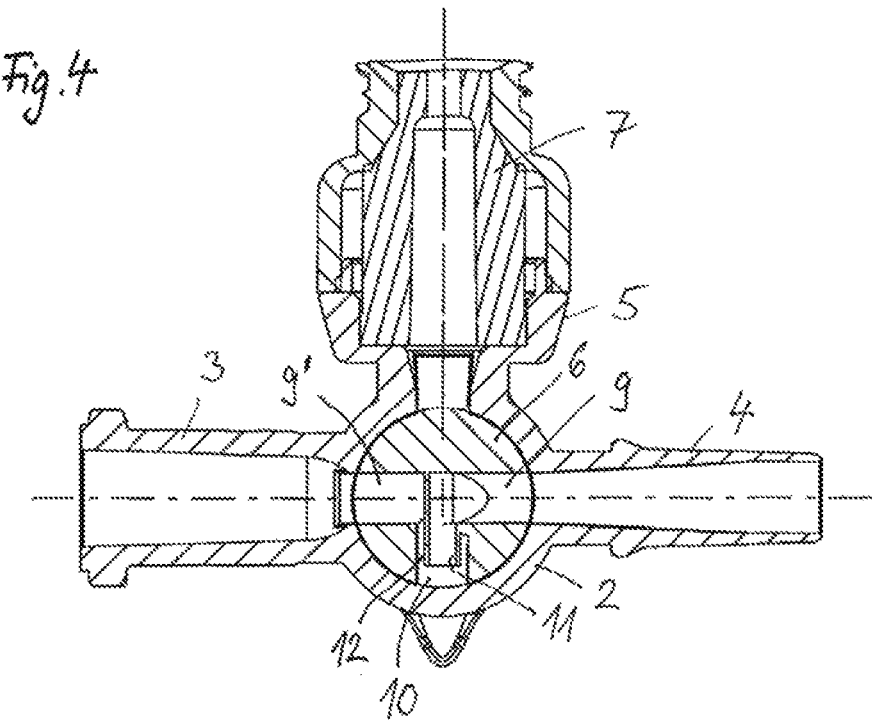
Figure 5:
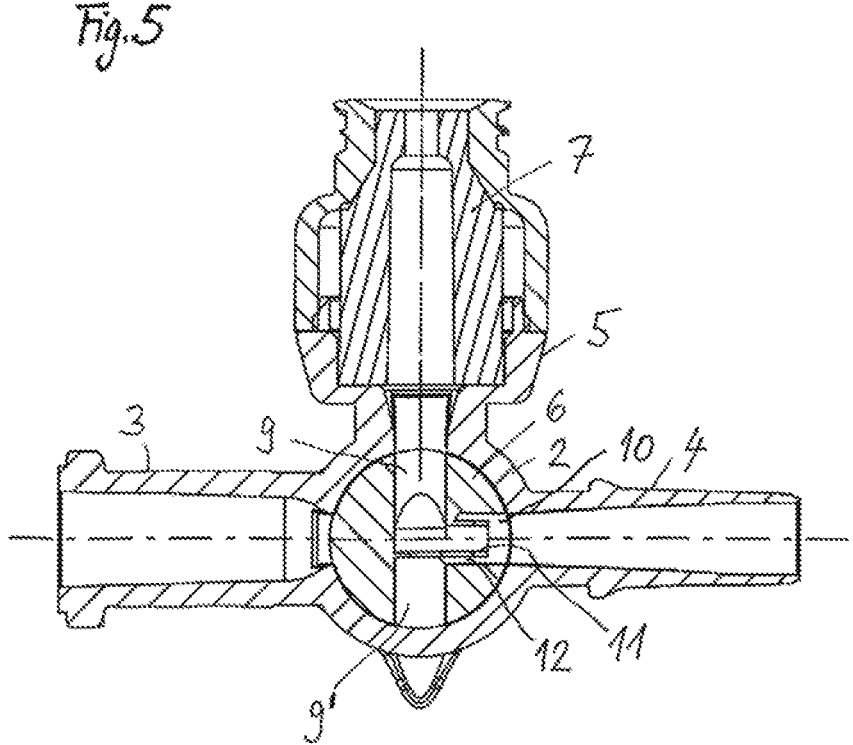
Figure 6:
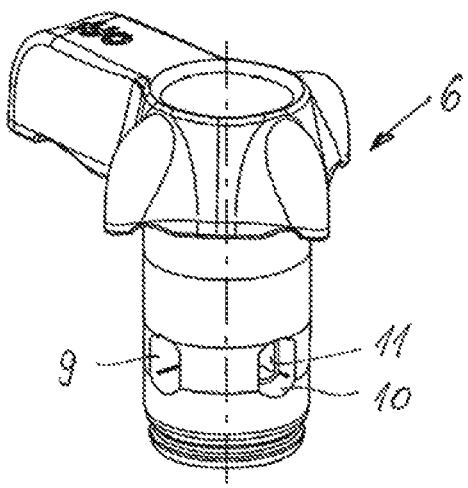
Figure 7:
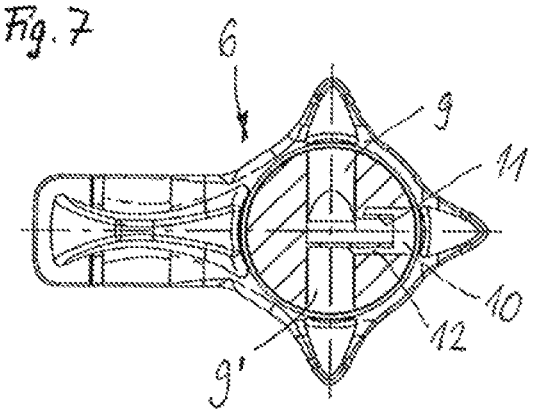
Figure 8:
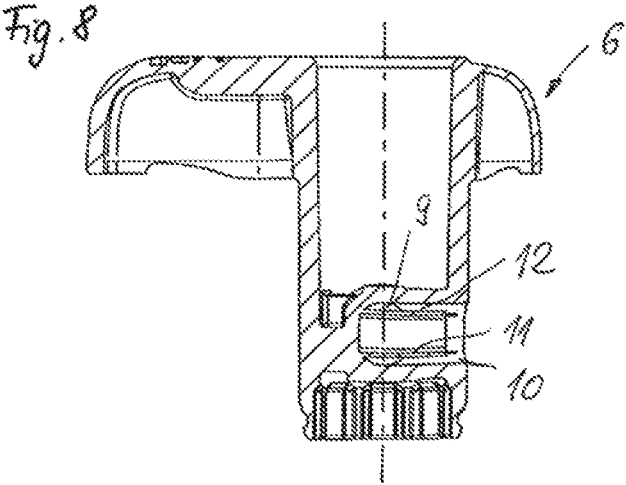
Figure 9:
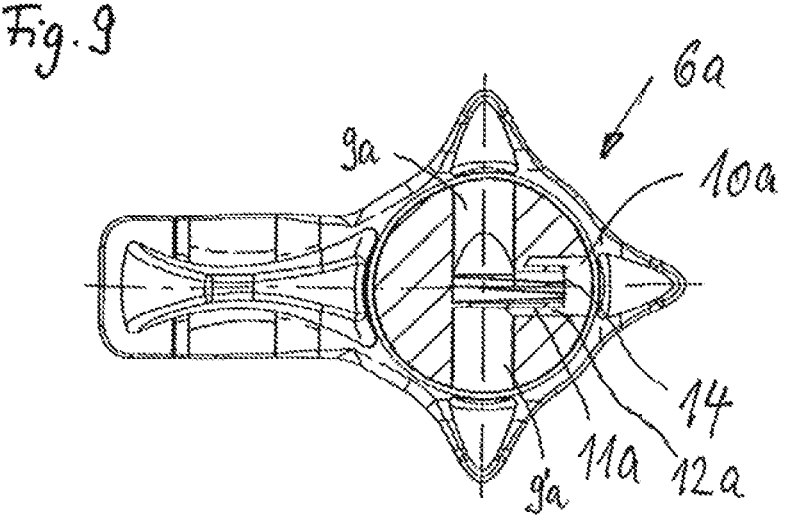
Figure 10:
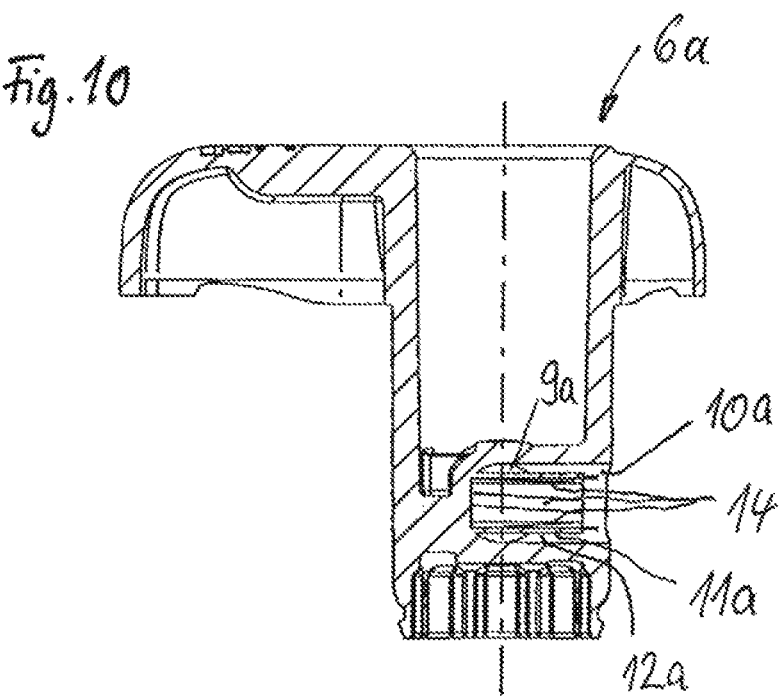

Further advantages and features emerge from the following description of preferred exemplary embodiments which are illustrated on the basis of the drawings, in which:

FIG. 1 shows a perspective exploded illustration of an embodiment of a medical fluid control device according to the invention in the form of a three-way stopcock, FIG. 2 shows a cross-sectional illustration of the three-way stopcock according FIG. 1 in a first functional position, FIGS. 3 to 5 show cross-sectional illustrations of the three-way stopcock according to FIGS. 1 and 2 in further functional positions, FIG. 6 shows a perspective illustration of an adjustment member of the three-way stopcock according to FIGS. 1 to 5, FIG. 7 shows a cross section through the adjustment member according to FIG. 6 at the height of flow channel sections of the adjustment member, FIG. 8 shows a longitudinal section through the adjustment member according to FIGS. 6 and 7, FIG. 9 shows a cross section through a further embodiment of an adjustment member similar to FIGS. 6 and 7, FIG. 10 shows a longitudinal section through the adjustment member according to FIG. 9 according to the longitudinal section according to FIG. 8.

Figure 11:
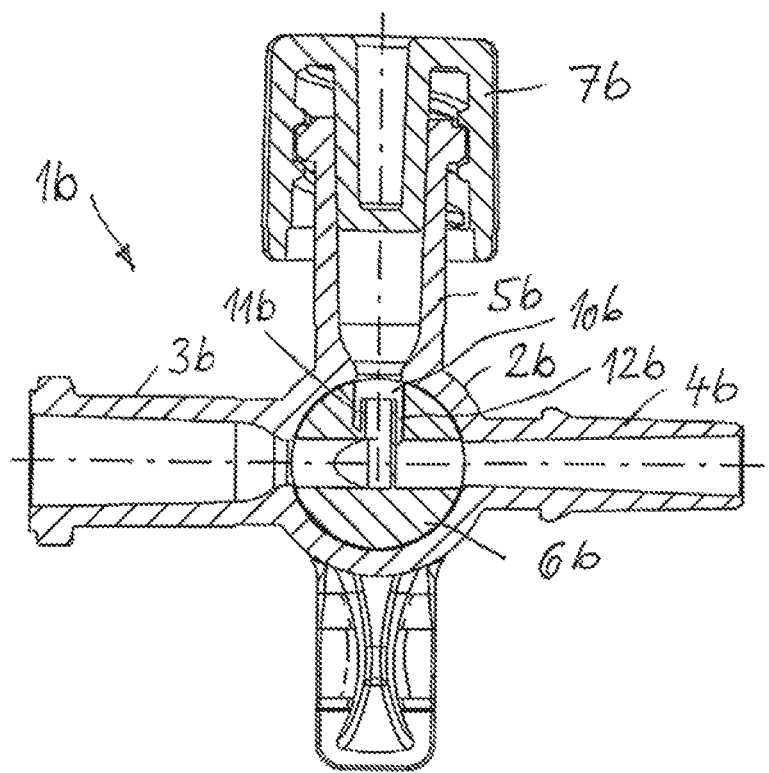

FIG. 11 shows, in a cross section, a further embodiment of a medical fluid control device according to the invention, FIG. 12 shows a further embodiment of a medical fluid control device according to the invention similar to FIG. 2, FIG. 13 shows a partially sectioned side view of the medical fluid control device according to FIG. 12 along the section line XIII-XIII in FIG. 12, and FIG. 14 shows a perspective illustration of the medical fluid control device according to FIGS. 12 and 13 with the omission of a closure diaphragm in the region of an injection port.

DETAILED DESCRIPTION

A medical fluid control device according to FIGS. 1 to 8 is designed as a three-way stopcock and is intended for use in a medical fluid line system in the form of an infusion system. The three-way stopcock 1 has a fluid flow housing 2 which consists of plastic, preferably of polyamide or polycarbonate, and is of hollow-cylindrical design. Mounted rotatably in the fluid flow housing 2 is an adjustment member 6 which is also referred to as a cock plug. In the region of a top side (FIG. 1), the adjustment member 6 is provided with an actuation handle in order to allow manual rotation of the adjustment member 6 inside the fluid flow housing 2 between different functional positions. In the region of a bottom side, the adjustment member 6 is provided with locking means (not depicted in any further detail) in order to secure the adjustment member 6 axially in the fluid flow housing 2. Such locking means for securing the adjustment member 6 are known through the applicant's U.S. Pat. No. 6,536,742 B2.

The fluid flow housing 2 has in a radial plane—relative to an axis of rotation of the adjustment member 6 as seen in the fluid flow housing 2—three ports which extend radially from the fluid flow housing 2 in different directions and from which there are formed two ports, diametrically opposite one another, as connection ports 3, 4 and one port, extending at right angles to said connection ports 3, 4, as an injection port 5. Both the connection ports 3, 4 and the injection port 5 are formed integrally on the fluid flow housing 2. The connection port 3 is provided with external Luer lock profilings on its end-side end region, which is remote relative to the fluid flow housing 2, for the connection to a complementary Luer lock connection part which is part of a further functional component of the medical fluid line system. The connection port 4 serves for connecting to a patient line, that is to say to a fluid line which is connectable to a patient intravenously or parenterally or in some other way.

Assigned to the injection port 5 is an openable closure element in the form of an elastically flexible closure diaphragm 7 which is positioned in a cup-shaped manner in a receptacle housing 8 which, in a fitted state, is securely connected to the injection port 5 and consequently forms a partial section of the injection port. The receptacle housing 8 is provided with a female Luer lock connection profiling on its end-side end region which is remote from the fluid flow housing 2 in order to allow the connection of a complementary Luer lock component which is in particular formed as part of an injector.

Alternatively, in an embodiment of the invention which is not illustrated, provision is made to provide a female Luer lock connection, which can interact with a male Luer connection of an injector by straightforward axial insertion of the male Luer connection, instead of an openable closure element at the receptacle housing.

Fluids in the form of medicaments can be dosed to the patient line via the injection port 5. For this purpose, a corresponding injector or another functional component is connected to the injection port 5 by means of the Luer lock connections, whereby the closure diaphragm 7 is necessarily deformed elastically and transferred into its open state. Following the injection of a corresponding dose of medicament, the injector or a corresponding other functional component can be removed from the injection port 5 again, whereby the closure diaphragm 7 is moved back into its closed position again.

In order to flush out medicament residue, which is still present in the region of the inside of the injection port 5, following the removal of a corresponding functional component from the injection port 5, a fluid throughflow, which is guided from a functional component that is permanently connected to the connection port 3 through the three-way stopcock 1, is diverted into the injection port 5 and subsequently guided further to the patient line via the connection port 4.

In order to improve flushing of the inside of the injection port 5 in the region of the inner wall of the injection port 5 and of an inner wall of the closure diaphragm 7, in the embodiments according to FIGS. 1 to 8, there is provided in the interior of the adjustment member 6 in the region of a flow channel section 10 a mechanical flow acceleration means in the form of a tube section 11 integrated into the flow channel section 10. The adjustment member 6 has in total three flow channel sections 9, 9', 10 which are provided at the height of the connection ports 3, 4 and of the injection port 5 in the adjustment member. The flow channel sections 9, 10, in dependence on the position of the adjustment member 6, serve for establishing between the connection ports 3, 4 and the injection port 5 fluid connections for a corresponding fluid throughflow. Different adjustment positions of the adjustment member 6 relative to the fluid flow housing 2 and thus different fluid paths between the connection ports 3, 4 and the injection port 5 are represented on the basis of FIG. 2 to 5.

A flushing position of the adjustment member 6 is set in FIG. 2. In this case, the mutually aligned flow channel sections 9, 9' of the adjustment member 6 extend, in coaxial connection, in a straight line between the connection ports 3, 4 which are situated opposite one another, whereas the flow channel section 10, at right angles thereto, is coaxially aligned with the interior of the injection port 5. In this functional position, the tube section 11 too is open toward the injection port 5. Here, it can be seen that the flow channel section 9, open toward the connection port 3, of the adjustment member 6 is diverted through a right angle into the tube section 11, the latter having a smaller flow cross section than the flow channel section 9. In the illustrated embodiment, the flow channel sections 9 and the flow channel section 10 of the adjustment member 6 have flow cross sections which are identical to one another. In embodiments of the invention not illustrated, the flow channel sections may have different flow cross sections, wherein in particular the flow cross section of the flow channel section 10 is larger than the flow cross section of the flow channel section 9. The tube section 11 is formed integrally in the adjustment member 6 which is preferably produced from a plastic, advantageously in the form of polycarbonate or polyamide, analogously to the fluid flow housing 2. In the region of its outer shell, the tube section 11 is at a distance from an inner wall of the flow channel section 10, which results in an annular gap 12 between the outer shell of the tube section 11 and the inner wall of the flow channel section 10. The flow channel section 10 is open via the annular gap 12 toward the flow channel section 9' which faces in the direction of the connection port 4 in FIG. 2. The corresponding annular gap 12 consequently allows continued guidance of the fluid throughflow, which is flushed through the tube section 11 into the interior of the injection port 5, to the connection port 4. By contrast, the flow channel section 9 is closed toward the opposite flow channel section 9', and so fluid which is fed via the inlet-side connection port 3 according to FIG. 2 can only be guided into the injection port 5 via the tube section 11 and from there guided to the outlet-side connection port 4 via the annular gap 12 and the diametrically opposite flow channel section 9'.

In FIG. 3, the adjustment member 6 is rotated relative to the fluid flow housing 2 in such a way that the tube section 11 is directed toward the connection port 3, whereas the flow channel section 9', which is open toward the flow channel section 10 via the annular gap 12, faces toward the injection port 5. The connection port 4 is closed by the adjustment member 6.

In FIG. 4, the adjustment member 6 is rotated such that the injection port 5 is closed and a coaxial fluid throughflow between the two connection ports 3, 4 via the flow channel sections 9, 9' is realized. The flow channel section 10 is positioned diametrically opposite the injection port 5 in the fluid flow housing 2. A fluid throughflow from the connection port 3 in the direction of the connection port 4 therefore takes place via the flow channel section 9', the annular gap 12 into the flow channel section 10 and from there via the tube section 11 into the adjoining flow channel section 9 which is open toward the connection port 4.

In FIG. 5, the adjustment member 6 is rotated such that the connection port 3 is closed, whereas the one flow channel section 9 is open toward the injection port 5, and the flow channel section 10 is open toward the connection port 4. The tube section 11 too is aligned coaxially with a central longitudinal axis of the connection port 4. This functional position of the adjustment member 6 corresponds to an injection position in which it is possible to feed a medicament solution to the patient line via the injection port 5.

The functional position according to FIG. 2 corresponds to a flushing position of the adjustment member 6 in which a fluid fed via the connection port 3 can flush out the inside of the injection port 5 and of the closure diaphragm 7 and is guided further to the outlet-side connection port 4 which is connected to the patient line.

On the basis of FIGS. 6 to 8, the adjustment member 6 is illustrated once more without the fluid flow housing 2 and the corresponding ports 3 to 5.

The adjustment member 6a according to FIGS. 9 and 10 corresponds substantially to the adjustment member 6 according to FIGS. 1 to 8, which has already been described in detail above. As an alternative to the adjustment member 6, the adjustment member 6a may be inserted into the fluid flow housing 2 of the three-way stopcock 1 according to FIGS. 1 to 8. In the case of the adjustment member 6a, a significant difference is that the tube section 10a is additionally provided with swirl-generating geometries 14 in the region of its inner wall. In the illustrated exemplary embodiment, the swirl-generating geometries 14 are formed integrally on corresponding inner-wall sections of the tube section 11a and bring about additional swirl generation on the fluid throughflow which can result in a further increase in the flow speed of the fluid throughflow. In embodiments of the invention not illustrated, swirl-generating geometries may be provided on separately produced structural parts which are detachably or non-detachably introduced into corresponding tube sections. This can further improve flushing of the injection port 5. The swirl-generating geometries 14 are in particular designed as helically-formed wall profilings. It is also possible to provide wall profilings formed differently. As a result, outer flow regions of the fluid throughflow should be diverted in the circumferential direction, whereby overall a swirl function is achieved for the fluid throughflow.

The medical fluid control device according to FIG. 11 represents a three-way stopcock 1b which is substantially of identical design to the embodiment described on the basis of FIGS. 1 to 8. In order to avoid repetition, reference is therefore made to the disclosure with respect to FIGS. 1 to 8. Functionally or structurally identical parts and sections of the three-way stopcock 1b are provided with identical reference signs with addition of the letter b.

The only difference of the three-way stopcock 1b from the three-way stopcock 1 according to FIGS. 1 to 8 is that the injection port 5b is provided not with a closure element in the form of a closure diaphragm but rather with a closure element in the form of a closure cap 7b. The closure cap 7b is provided with male Luer lock connection profiles, whereas the injection port 5b is formed with complementary female Luer lock connection profiles. An operator can screw the closure cap 7b onto the injection port 5b or remove it from this by a simple rotational movement, wherein a cone section of the closure cap 7b engages in a sealed manner in a receptacle opening of the injection port 5b.

In the embodiment according to FIGS. 12 to 14, provision is made for a three-way stopcock 1c which corresponds substantially to the embodiment described above on the basis of FIGS. 1 to 8. In order to avoid repetition, reference is therefore additionally made to the disclosure with respect to the embodiment according to FIGS. 1 to 8. Identical parts and sections of the three-way stopcock 1c are provided with identical reference signs with addition of the letter c. In the following text, the differences from the embodiment according to FIGS. 1 to 8 will be addressed. In the embodiment according to FIGS. 12 to 14, a significant difference is that an additional mechanical flow acceleration means, which is formed as a tube section 13, is integrated in the injection port 5c. The tube section 13 is formed integrally in a partial section of the fluid flow housing 2c, which partial section forms part of the injection port 5c. Said part of the injection port 5c forms a receiving connector for fastening the receptacle housing 8c, wherein the receiving connector and the receptacle housing 8c surround the closure diaphragm 7c. The tube section 13 is integrated in a channel section 15 of the receiving connector of the injection port 5c and is connected integrally to a wall of the channel section 15. For this purpose, the tube section 13 has on its top side a connection web 16 which suspends the tube section 13 in the channel section 15 of the injection port 5c. The tube section 13 is formed together with the channel section 15 and the connection web 16 and also the fluid flow housing 2c in a corresponding production process, in particular a plastic injection-molding process, and is integrally connected to the fluid flow housing 2c via the connection web 16. The connection ports 3c, 4c are likewise formed integrally on the fluid flow housing 2c. A tube cross section of the tube section 13 is identical to the tube cross section of the tube section 11c which is formed in the adjustment member 6c. The two tube sections 11c and 13 have flow cross sections which are identical to one another. Based on FIG. 13, it can be seen that the tube section 13 has a rotationally asymmetrical cross section. The tube section 13 and the tube section 11c which corresponds to the tube sections 11 and 11b according to FIGS. 1 to 11 have two wall sections which are horizontally opposite one another and parallel to one another and which in each case merge at the top and bottom into two wall sections of arcuately curved cross section. Also consider a rotationally symmetrical cross section (circle). The height extent of the flow cross section is—as can be seen from FIG. 13—larger than a transverse extent of the flow cross section of the respective tube section 13 or 11, 11a, 11b, 11c. According to embodiments of the invention which are not illustrated, it is also possible for the tube section 13 to be connected integrally to the receiving connector of the injection port 5c via a plurality of connection webs arranged so as to be distributed over the circumference of said tube section. Alternatively, the tube section 13 is held via a single connection web in the channel section 15 of the injection port 5c, which web, in a correspondingly different embodiment of the invention, however, is not positioned in the region of the top side, but in the region of a bottom side or in the region of an outer side pointing to the left or to the right according to FIG. 13.

The invention claimed is:

1. A medical fluid control device for a medical fluid line system, the medical fluid control device comprising:
    a fluid flow housing having a cylindrical inner chamber with an inlet-side connection port, an outlet-side connection port for connecting to a further functional component of the fluid line system, and an injection port which is provided with an openable closure element, wherein the inlet-side connection port and outlet-side connection port are located on opposite sides of the cylindrical inner chamber, and the injection port is oriented at 90 degrees relative to the inlet-side connection port and the outlet-side connection port with respect to a rotation axis of the cylindrical inner chamber;
    an adjustment member movably mounted within the cylindrical inner chamber and configured to rotate about the rotation axis of the cylindrical inner chamber, the adjustment member having:
        a first flow channel section extending into the adjustment member at a first location, a second flow channel section extending into the adjustment member at a second location located opposite the first location, and a third flow channel section extending into the adjustment member at a third location, the third location being oriented at 90 degrees relative to the first location and second location with respect to the rotation axis of the cylindrical inner chamber,
    wherein the adjustment member is movable about the rotation axis of the cylindrical inner chamber between at least:
        a first position in which the first flow channel section faces the inlet-side connection port, the second flow channel section faces the outlet-side connection port and the third flow channel section faces the injection port, and
        a second position in which the first flow channel section faces the injection port, the second flow channel section faces a portion of the cylindrical inner chamber opposite the injection port, and the third flow channel section faces the outlet-side connection port; and
    a first mechanical flow acceleration means located within the third flow channel section of the adjustment member, the first mechanical flow acceleration means being configured to assist with inside flushing of the injection port during a fluid throughflow when the adjustment member is in the first position;
wherein:
    the third flow channel section comprises a channel wall defining a first longitudinal axis,
    the first mechanical flow acceleration means comprises a tube wall inside the channel wall that defines a second longitudinal axis, and
    the second longitudinal axis is coaxial in its entirety with the first longitudinal axis.

2. The medical fluid control device of claim 1, wherein the tube wall is integrated into the third flow channel section and has a respective flow cross section that is smaller than a respective flow cross section of the inlet side connection port, the injection port, or the outlet-side connection port.

3. The medical fluid control device of claim 2, wherein the tube wall is formed integrally in the third flow channel section.

4. The medical fluid control device of claim 2, wherein an annular gap allowing a fluid throughflow is provided between an outer wall of the tube wall and a wall of the surrounding third flow channel section.

5. The medical fluid control device of claim 2, wherein an inner wall of the tube wall comprises swirl-generating geometries configured to act on the fluid throughflow.

6. The medical fluid control device of claim 1, wherein the outlet-side connection port defines a third longitudinal axis, and wherein the first longitudinal axis and the second longitudinal axis are coaxially aligned with the third longitudinal axis when the adjustment member is in the second position.

7. The medical fluid control device of claim 6, wherein the injection port defines a fourth longitudinal axis, and wherein the first longitudinal axis and the second longitudinal axis are coaxially aligned with the fourth longitudinal axis when the adjustment member is in the first position.

8. The medical fluid control device of claim 1, wherein the tube wall is connected to the channel wall by a web.

9. The medical fluid control device of claim 1, wherein the tube wall is radially spaced from the channel wall on all sides.

10. The medical fluid control device of claim 1, further comprising a second mechanical flow acceleration means located within the injection port.

* * * * *